United States Patent
Chen et al.

(10) Patent No.: US 12,268,600 B2
(45) Date of Patent: Apr. 8, 2025

(54) METHOD FOR RESHAPING SEVERELY STENOSED AORTIC VALVE HAVING LEAFLETS WITH BICUSPID MALFORMATION AND SEVERE CALCIFICATION

(71) Applicant: VENUS MEDTECH (HANGZHOU) INC., Zhejiang (CN)

(72) Inventors: Mao Chen, Zhejiang (CN); Yuan Feng, Zhejiang (CN); Zhenjun Zi, Zhejiang (CN); Zhengang Zhao, Zhejiang (CN); Hou-Sen Lim, Zhejiang (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 924 days.

(21) Appl. No.: 17/426,317

(22) PCT Filed: Jan. 29, 2019

(86) PCT No.: PCT/CN2019/073791
§ 371 (c)(1),
(2) Date: Jul. 28, 2021

(87) PCT Pub. No.: WO2020/154928
PCT Pub. Date: Aug. 6, 2020

(65) Prior Publication Data
US 2022/0096228 A1    Mar. 31, 2022

(51) Int. Cl.
*A61F 2/24*    (2006.01)
(52) U.S. Cl.
CPC .................. *A61F 2/2433* (2013.01)

(58) Field of Classification Search
CPC .............................. A61F 2/2433; A61F 2/243
See application file for complete search history.

(56) References Cited

U.S. PATENT DOCUMENTS

| 6,730,118 B2 * | 5/2004 | Spenser | A61F 2/2436 |
| | | | 623/1.24 |
| 7,748,389 B2 * | 7/2010 | Salahieh | A61F 2/2439 |
| | | | 623/2.14 |

(Continued)

FOREIGN PATENT DOCUMENTS

WO    WO-2013184945 A1 * 12/2013    ........... A61B 18/082

OTHER PUBLICATIONS

Transcatheter Aortic Valve Implantation for Patients With Severe Bicuspid Aortic Valve Stenosis; Hayashida et al. (Year: 2013).*

(Continued)

*Primary Examiner* — Erin McGrath

(57) ABSTRACT

A method of reshaping a severely stenosed aortic valve having leaflets with bicuspid malformation and severe calcification. The method includes delivering a balloon with an expandable distal end to the aortic valve, expanding the balloon so that the distal end of the balloon is expanded to push the leaflets upward from bottom of the aortic valve to reshape the leaflets, and forming a space compliant to a self-expandable interventional valve for release, thereby facilitating the following TAVR procedure, reducing the adverse consequences of the TAVR procedure, and improving the surgical stability and the surgical prognosis.

15 Claims, 9 Drawing Sheets

(56) References Cited

U.S. PATENT DOCUMENTS

| | | | | |
|---|---|---|---|---|
| 2005/0075662 A1* | 4/2005 | Pedersen | ............... | A61M 25/10 |
| | | | | 977/875 |
| 2013/0144328 A1* | 6/2013 | Weber | ............... | A61M 25/0074 |
| | | | | 606/200 |
| 2015/0306359 A1* | 10/2015 | Drasler | ................ | A61F 2/2433 |
| | | | | 606/191 |

OTHER PUBLICATIONS

Predictors for permanent pacemaker implantation in patients undergoing transfemoral aortic valve implantation with the Edwards Sapien 3 valve, Gonska et al. (Year: 2017).*

Written Opinion for PCT/CN2019/073791 dated Oct. 15, 2019, (5 pages).

* cited by examiner

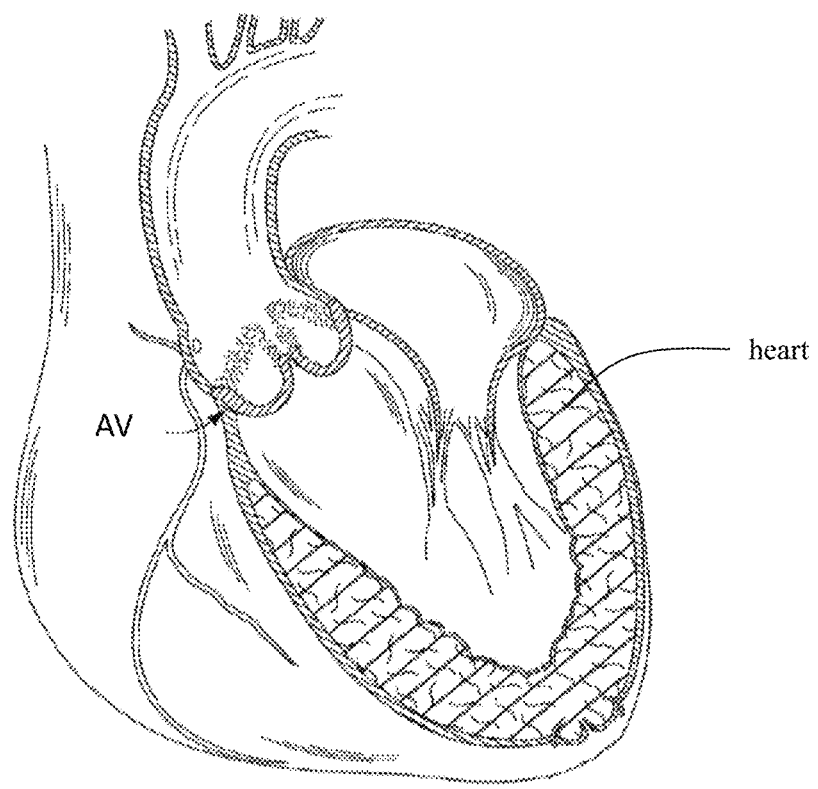
FIG. 1a
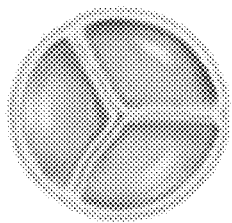 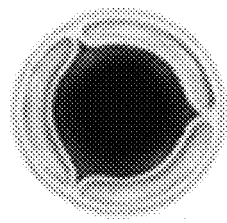 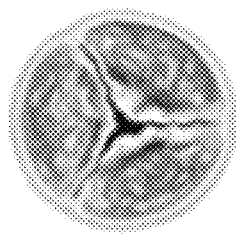 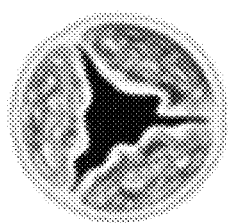
FIG. 1b　　FIG. 1c　　FIG. 1d　　FIG. 1e

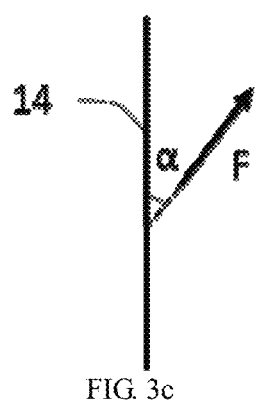
FIG. 3c
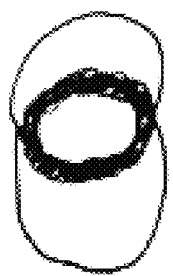  
A-A  B-B  C-C
FIG. 4a  FIG. 4b  FIG. 4c before reshaping after reshaping

METHOD FOR RESHAPING SEVERELY STENOSED AORTIC VALVE HAVING LEAFLETS WITH BICUSPID MALFORMATION AND SEVERE CALCIFICATION

TECHNICAL FIELD

The present disclosure relates to the treatment for aortic stenosis, and to a method for reshaping a stenosed aortic valve having leaflets with bicuspid malformation and severe calcification.

BACKGROUND

Aortic stenosis (AS) is a very common disease in people over 70 years of age, and the incidence of AS tends to increase with age. Transcatheter Aortic Valve Replacement (TAVR) has become the primary treatment method for the elderly patients and/or patients with moderate to severe aortic stenosis (AS).

The Bicuspid Aortic Valve (BAV) is the most common congenital cardiac malformation, with an incidence of about 0.5% to 2% in the general population. BAV is an important pathogeny of aortic stenosis (AS). In contrast to normal tricuspid aortic valve, BAV has a higher risk of degenerative calcification due to the special configuration of its leaflets under a greater mechanical stress. Patients with severe valvular stenosis tend to be younger and younger. For a long time, BAV has been regarded as the relative contraindication of TAVR, and early TAVR clinical studies exclude BAV due to the significant difference between the configuration of the leaflets of the stenotic BAV and the stenotic tricuspid aortic valve. The BAV leaflets have a shape of "volcanic vent" from the root of the leaflets (annulus) to the top of the leaflets (orifice). The interior space of the BAV leaflets for TAVR valve expansion is bounded by the leaflets and has a gradually reduced circumference and area, with a long elliptic shape. The area of the annulus does not conform to the area of the orifice, and the circumference of the orifice is approximately equal to two thirds of the circumference of the annulus. Moreover, the BAV leaflets of a patient usually have severe or extremely severe calcification, asymmetric calcification, fusion and/or calcification at the commissures of the leaflets, and the calcified portions of the leaflets usually extend to the annulus and the left ventricular outflow tract.

For TAVR, the above anatomical features of BAV may mainly cause the following problems.

(1) In the initial stage of releasing the self-expandable TAVR valve, the inflow end (bottom end) of the self-expandable TAVR valve has a normal cone shape, and the BAV leaflets with severe calcification and having a "volcanic vent" shape are also similar to the normal cone shape with poor compliance. Therefore, during the interaction between the self-expandable TAVR valve and the BAV leaflets, the latter may exert a downward force (toward left ventricle) on the former, and the force which is difficult to be adjusted and controlled by the operator would cause the TAVR valve to be excessively displaced and implanted, resulting in an obvious perivalvular leakage, implantation of another valve, or even surgical thoracotomy.

(2) The implanted TAVR valve (even a balloon-expandable valve with strong supporting force) may be expanded poorly and/or deformed obviously being constrained by severely calcified leaflets as well as the fused or calcified commissures of leaflets, thereby affecting the immediate hemodynamic effect and long-term durability of the valve.

An existing method of reshaping the aortic valve is to reshape BAV by using a cylindrical balloon which has a long length acting on the left ventricular outflow tract. In order to reduce the risk of rupture of the valve annulus, a smaller size of balloon is usually selected, which will result in insufficient expansion. In addition, the expansion of the cylindrical balloon requires rapid ventricular pacing, which may result in hemodynamic disturbance in patient with poor left ventricular function.

SUMMARY

In view of this, it is necessary to provide a method of reshaping a severely stenosed aortic valve having leaflets with bicuspid malformation and severe calcification, which can solve the above problems.

The present disclosure provides a method of reshaping a severely stenosed aortic valve having leaflets with bicuspid malformation and severe calcification, including delivering a balloon with an expandable distal end to the aortic valve, expanding the balloon so that the distal end of the balloon is expanded to push the leaflets upward from bottom of the aortic valve to reshape the leaflets, and forming a space compliant to a self-expandable interventional valve for release.

In some embodiments, the leaflets of the aortic valve generally have a severe or extremely severe calcification, with a volume exceeding 500 mm$^3$ detected using HU-850 as a threshold.

In some embodiments, the calcification of the leaflets of the aortic valve is mainly distributed at the main bodies and free edges of the leaflets, and is distributed symmetrically.

In some embodiments, according to a semi-quantitative assessment, the difference in grades of calcification degree of the leaflets on two sides of the aortic valve is smaller than 2.

In some embodiments, there are moderate to severe, calcified mass protruding towards the cavity at level of the annulus and the left ventricular outflow tract of the aortic valve.

In some embodiments, the leaflets of the aortic valve have moderate to severe calcification at commissures of the leaflets.

In some embodiments, the balloon is configured to pass through the orifice of the aortic valve and extend at least to the bottom of the aortic valve, and a portion of the balloon located at the orifice has a smaller diameter than a portion of the balloon resting on the main bodies of the leaflets.

In some embodiments, the distal end of the balloon is configured to abut the bottom side of the aortic valve after being expanded, and support and expand the leaflets in a direction at an acute angle to a proximal end of an axis of the balloon.

In some embodiments, the acute angle is in a range of 20-70 degrees, which may be in the range of 30-60 degrees.

In some embodiments, the direction is substantially perpendicular to the main bodies of the leaflets.

In some embodiments, the distal end of the balloon is configured to support and expand the leaflets for 3-5 seconds after being expanded, which may be 4 seconds.

In some embodiments, a force to the main bodies of the leaflets from the expanded balloon is greater than a force to the orifice of the aortic valve from the expanded balloon.

In some embodiments, a maximum force to the leaflets from the expanded balloon is located at a position of 2-8 mm from the annulus to the orifice.

In some embodiments, the force to the orifice from the expanded balloon is greater than a force to the annulus of the aortic valve from the expanded balloon.

In some embodiments, a force to the annulus from the expanded balloon is zero.

In some embodiments, the reshaped leaflets of the aortic valve have a concaved arc-shaped inner surface.

In some embodiments, the balloon further comprises an expandable proximal end and a waist between the distal end and the proximal end, wherein after the balloon is expanded, the waist has a smaller size than the distal end and the proximal end, and the balloon is positioned so that the waist corresponds to the orifice of the aortic valve.

In some embodiments, materials of the waist and the proximal end of the balloon are more compliant than a material of the distal end of the balloon.

In some embodiments, when the balloon is expanded, the balloon is first inflated at a first pressure so that the distal end is fully expanded, and the proximal end has a smaller diameter than the orifice at the first pressure, and the balloon is continually inflated at a second pressure so that the proximal end is fully expanded, wherein the second pressure is greater than the first pressure.

In some embodiments, the maximum diameter of the distal end of the balloon is greater than or equal to the maximum diameter of the proximal end of the balloon.

In some embodiments, the balloon is loaded into a delivery system prior to the delivering, and the delivery system delivers the balloon to the aortic valve via a trans-femoral puncture course.

In some embodiments, the distal end of the expanded balloon is spherical, hemispherical, ellipsoidal or drop-like.

In some embodiments, the balloon further comprises at least one marker for indicating position of the balloon.

The method of reshaping the aortic valve according to the present disclosure adopts a balloon with an expandable distal end which is expanded so that the distal end of the balloon is expanded to push the leaflets upwards from the bottom of the aortic valve to reshape the leaflets, to form a space compliant to the self-expandable interventional valve implanted in the following TAVR procedure for release, thereby facilitating the following TAVR procedure, reducing the adverse consequences of the TAVR procedure, and improving the surgical stability the surgical prognosis.

BRIEF DESCRIPTION OF THE DRAWINGS

FIG. 1a is a schematic perspective view of the human heart showing the position of the aortic valve.

FIGS. 1b and 1c are schematic top views of a normal tricuspid aortic valve in a closed and open state, respectively.

FIGS. 1d and 1e are schematic top views of a calcified and stenosed tricuspid aortic valve in a closed and open state, respectively.

FIG. 3c schematically shows the direction of the abutment force against the leaflets from the distal end of the expanded balloon.

FIGS. 4a-4c are schematic top views of openings of the aortic valve at positions indicated by the letters A-C in FIG. 3b after the aortic valve is expanded using the method shown in FIGS. 3a-3b.

DETAILED DESCRIPTION

Figure 2A:
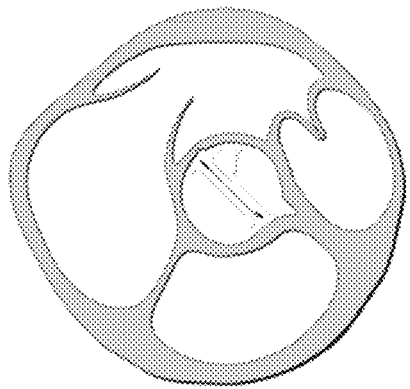
FIGS. 2a and 2b are schematic top views of a bicuspid aortic valve without stenosis in a closed and open state, respectively.

In the following, the present disclosure will be described in detail with reference to the accompany drawings and specific embodiments to make the subject matter of the present application and the technical effects thereof more clear. It is to be understood that the drawings are only for reference and illustration, and are not intended to limit the application, and the dimensions shown in the drawings are only for clarity of description and are not intended to limit the proportionality.

Referring to FIGS. 1a-1e, the leaflets of normal tricuspid aortic valve are soft and flexible, the tips of which leaflets, in the open condition, enclose a large orifice, so that blood can smoothly pass therethrough. In the case where valve stenosis occurs due to calcification of leaflets, the diameter of the orifice enclosed by the leaflets in the open condition is seriously reduced, thereby blocking the blood flow and affecting the normal operation of the heart.

Figure 2B:
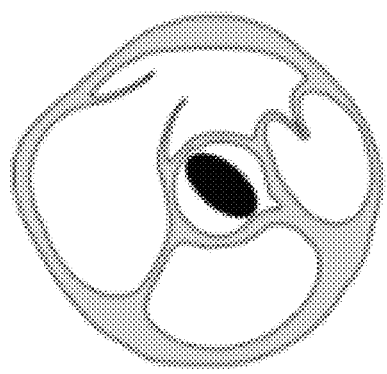
Figure 2C:
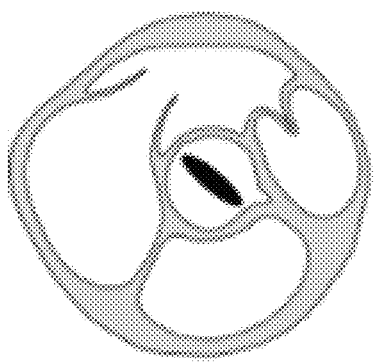
FIG. 2c is a schematic top view of a calcified and stenosed bicuspid aortic valve in an open state.

FIGS. 2a-2c show bicuspid aortic valves (BAV). As can be seen from FIG. 2b, the leaflets of the bicuspid aortic valve without stenosis, in the open condition, enclose an oval orifice, and the orifice of BAV without stenosis has an area significantly smaller than that of the tricuspid aortic valve. As can be seen from FIG. 2c, in the case where the bicuspid aortic valve has severe stenosis due to severe calcification, the orifice of the BAV has an oval shape with a greater difference between the major axis and the minor axis thereof, which is very unfavorable for TAVR. Therefore, it is necessary to reshape the leaflets before TAVR, to improve the compliance of the leaflets and form a space for a self-expandable interventional valve to be implanted in the following TAVR procedure for release.

Figure 3A:
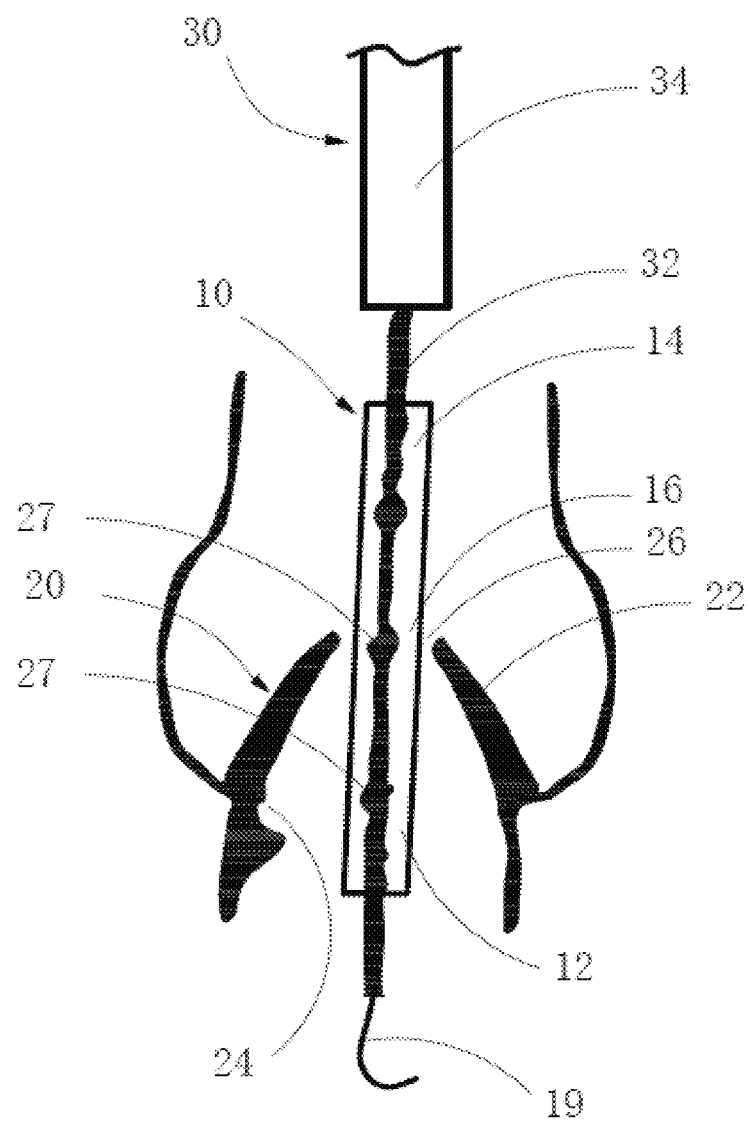
FIGS. 3a and 3b are schematic views showing the method of reshaping the leaflets of the aortic valve using an expandable balloon according to a first embodiment.
Figure 3B:
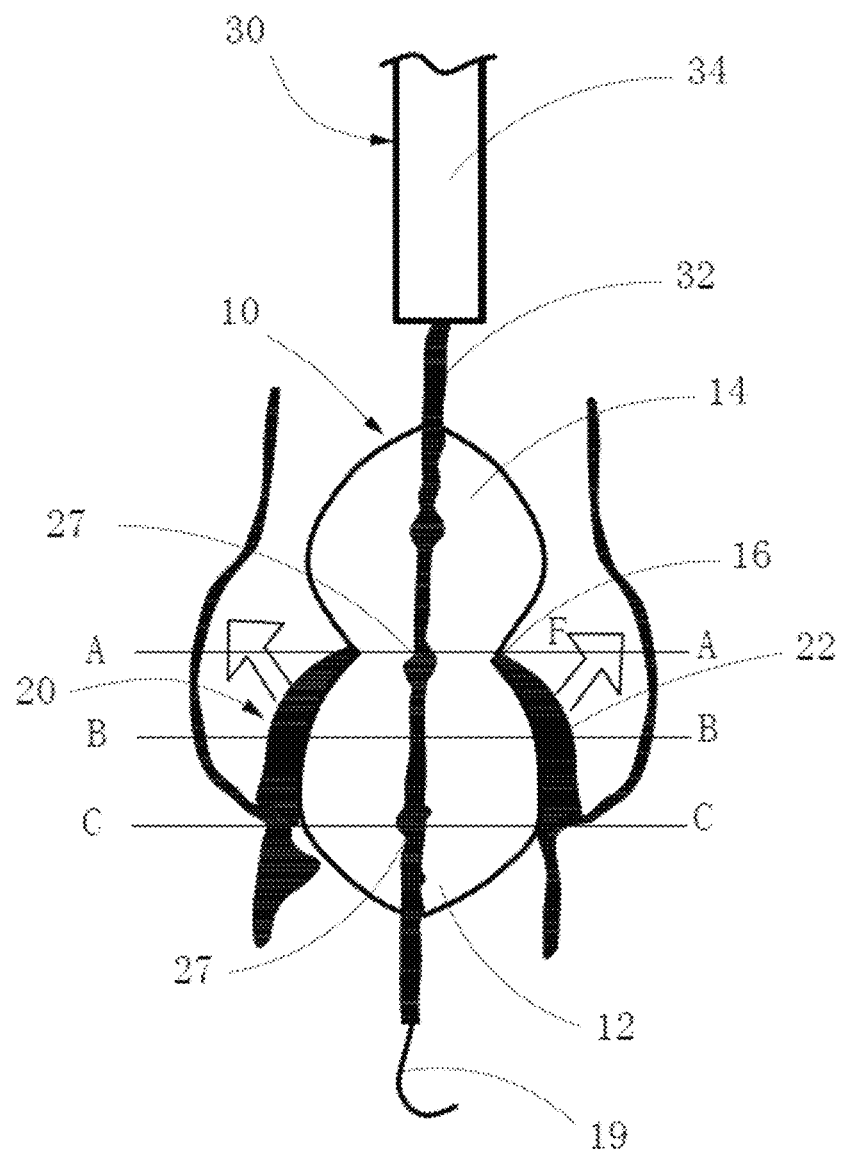

FIGS. 3a and 3b show a method of reshaping leaflets of a severely stenosed aortic valve according to the first embodiment, the leaflets of which have bicuspid malformation and severe calcification. The method mainly includes: delivering an expandable balloon 10 having an expandable distal end 12 to a severely stenosed aortic valve 20 having leaflets with bicuspid malformation and severe calcification; after delivering of the expandable balloon 10, expanding the distal end 12 of the expandable balloon 10 and pushing the leaflets 22 up from the bottom of the aortic valve 20 to reshape the leaflets 22, to form a space for a self-expandable interventional valve to be implanted in the following TAVR procedure for release. The method of the present disclosure reshapes a severely stenosed aortic valve 20 with severe calcification using the expandable balloon 10 to create a space for the self-expandable interventional valve to be implanted in the following TAVR procedure for release, thereby reducing the adverse consequences of TAVR procedure.

The leaflets of the aortic valve may generally have a severe or extremely severe calcification, with a volume exceeding 500 mm$^3$ detected using HU-850 as a threshold. The leaflets of the aortic valve mainly have calcification at the main bodies and the free edges thereof, and the distributions of the calcification are symmetric. According to a semi-quantitative assessment, the difference in the grades of calcification degree of the leaflets 22 on two sides of the aortic valve 20 is smaller than 2. In some cases, the aortic valve 20 has moderate to severe, calcified mass protruding towards the cavity at the level of the annulus 24 and the level of the left ventricular outflow tract. In some cases, the leaflets 22 of the aortic valve have moderate to severe calcification at the commissures of the leaflets.

The expandable balloon 10 may extend through the orifice 26 of the aortic valve 20 from the distal cardiac side of the orifice 26 and at least to the bottom of the aortic valve 20. The diameter of the portion of the expanded balloon 10 located at the orifice 26 is smaller than the diameter of the portion of the expanded balloon 10 supporting the main bodies of the leaflets 22. Therefore, the leaflets 22 can be fully expanded to improve the compliance thereof, and at the same time, the orifice 26 is merely moderately expanded to prevent the leaflets 22 to be torn and the structural integrity thereof to be broken, thereby reducing the risk of serious consequences such as acute aortic regurgitation and circulatory collapse after expansion.

The distal end 12 of the expanded balloon 10 abuts the downside of the aortic valve 20 and expands the leaflets 22 in a direction at an acute angle relative to the proximal end of the axis of the balloon 10. The acute angle may be in the range of 20-70 degrees, or in the range of 30-60 degrees. The direction in which the balloon 10 expands the leaflets 22 is substantially perpendicular to the main body of the leaflets 22.

In the method of the present disclosure, the distal end of the balloon 10 expands the leaflets 22 for 3-5 seconds, such as for 4 seconds.

In the embodiment shown in FIGS. 3a and 3b, the balloon 10 further includes an expandable proximal end 14. Both the distal end 12 and the proximal end 14 of the expanded balloon have a shape of ellipsoid, with the major axis of the ellipsoid coinciding with the longitudinal axis of the expanded balloon. The expanded balloon 10 has a waist 16 between the distal end 12 and the proximal end 14, with the diameter of the waist 16 being smaller than the diameters of the distal end 12 and the diameters of the proximal end 14. The maximum diameter of the distal end 12 is equal to or greater than the maximum diameter of the proximal end 14. Specifically, the distal end 12 has a maximum diameter of 21-29 mm, the proximal end 14 has a diameter of 20-28 mm, and the waist 16 has a diameter of 16-22 mm.

In operation, the expandable balloon 10 which has not been expanded yet is first delivered to the aortic valve 20, which may be through a trans-femoral delivery course. The expandable balloon 10 may be delivered using a guidewire 19. In the present embodiment, the expandable balloon 10 is loaded into a delivery system 30. The delivery system 30 includes a shaft tube 32 and a sheath 34 surrounding the shaft tube 32. The expandable balloon 10 is attached to the shaft tube 32 and received within the sheath 34. After the delivery system 30 is delivered to the predetermined location at the aortic valve 20, the sheath 34 is withdrawn to expose the expandable balloon 10.

Upon delivery of the expandable balloon 10, the distal end 12 of the balloon 10 passes through the orifice 26 and extends at least to the downside of the aortic valve 20. The expandable balloon 10 may be positioned with its waist 16 at the orifice 26, the distal end 12 and the proximal end 14 located at the proximal cardiac side of the orifice 26 and the distal cardiac side of the orifice 26, respectively.

The distal end 12 of the balloon 10 may be made of a non-compliant material, and the waist 16 and the proximal end 14 are made of compliant materials, that is, the materials of the waist 16 and the proximal end 14 are more compliant than the material of the distal end 12. In some cases, the balloon may be positioned through a difference in material compliance between the distal and proximal ends of the balloon, as well as staged inflation of the balloon. Specifically, the balloon is first inflated at a first small pressure, such as 1.5 atm, so that the non-compliant distal end 12 is expanded to its maximum diameter, with the proximal end 14 and the waist 16 unexpanded so that the diameters of the proximal end 14 and the waist 16 are smaller than the diameter of the orifice 26 (or slightly expanded so that the expanded diameters are smaller than the diameter of the orifice 26). The balloon 10 can be pulled back so that the proximal end 14 and the waist 16 pass smoothly through the orifice 26 without damage to the orifice 26 caused by pulling, until the distal end 12 abuts the proximal cardiac side of the orifice 26, the waist 16 is locked within the orifice 26, and the proximal end 14 is located on the distal cardiac side of the orifice 26, thus accurately positioning the expandable balloon 10 at the aortic valve 20.

The balloon 10 is then further inflated, at a second, greater pressure, such as 3 atm, to expand the proximal end 14 and the waist 16 of the balloon 10, with the waist 16 having a small diameter locked within the narrow orifice 26. As the waist 16 with a concaved configuration is firmly locked within the narrow orifice 26 without movement under the impact of the blood flow, there is no need to reduce cardiac output by rapid ventricular pacing to prevent the balloon from movement with the blood flow, which is contrary to the method of expanding the aortic valve using a conventional cylindrical balloon. The expanded proximal end 14 of the balloon 10 abuts against the distal cardiac side of the orifice 26. That is, the orifice 26 is sandwiched between the proximal end 14 and the distal end 12, which allows the balloon 10 to be locked at the aortic valve 20.

In order to accurately position the balloon 10, a radiopaque marker 27 may be provided on the balloon 10. The marker 27 is positioned at a location corresponding to the waist 16 of the balloon 10, for tracking the delivery position of the balloon 10 in real time during the procedure in conjunction with the fluoroscopy, so that the waist 16 can be accurately positioned at the orifice 26. In some embodiments, a plurality of markers can be provided, including the marker disposed corresponding to the waist 16, as well as other markers located corresponding to the shoulder of the distal end 12 of the balloon 10 (i.e., at a level where the distal end 12 has the largest diameter and closest to the ventricle)

to facilitate observation of this portion in correspondence with the aortic annulus 24 and the left ventricular outflow tract.

The distal end 12 of the balloon 10 is expanded to abut against the main bodies of the aortic leaflets 22 and apply an abutment force on the main bodies of the aortic leaflets 22. As shown in FIG. 3c, the abutment force applied by the distal end 12 of the balloon 10 against the main bodies of the leaflets 22 is not a radial force, that is, the abutment force is not perpendicular to the axis of the balloon 10. An acute angle α may be defined between the abutment force and the proximal end of the axis of the balloon 10, which may be in the range of 20-70 degrees, which may be 30-60 degrees. Thus, the distal end 12 of the balloon 10 expands the main bodies of the leaflets 22 upward and outward, to reshape the leaflets and improve the compliance of the leaflets. At the same time, the waist 16 with small diameter moderately expands the orifice 26 to prevent the leaflets 22 to be torn and the structural integrity thereof to be broken, thereby reducing the risk of serious consequences such as acute aortic regurgitation and circulatory collapse after expansion.

The expanded balloon 10 may provide the abutment force against the aortic valve 20 so that the abutment force is the maximum at the position of 2-8 mm from the valve annulus 24 to the orifice 26, and the second at the orifice 26, and the minimum or zero at the level of the annulus 24.

The maximum diameter of the distal end 12 of the balloon 10 may be located between the annulus 24 and the orifice 26 at a distance of about 2-8 mm from the annulus. In the cases where the distal end 12 of the balloon 10 does not come into contact with the annulus 24, the maximum size of the distal end 12 of the balloon 10 can be larger than the size of the annulus 24 for about 2 mm, to reshape the leaflets 22 more fully without causing damage to the annulus 24.

FIGS. 4a-4c show the relationship between the balloon 10 at the positions indicated by the letters A-C of the aortic valve in FIG. 3b and the root anatomy of the aortic valve after expansion of the aortic valve using the method shown in FIGS. 3a-3b, wherein FIGS. 4a, 4b and 4c correspond to the cross-sections at the levels indicated by the letters A (orifice 26), B (the main bodies of the leaflet 22) and C (the left ventricular outflow tract of the annulus 24) shown in FIG. 3b, respectively. As shown in FIG. 4a, the concaved waist 16 of the balloon 10 mainly functions to lock the balloon 10, and merely moderately expands the orifice 26 of the aortic valve, avoiding acute aortic regurgitation due to over expansion. As shown in FIG. 4b, the portion of the balloon 10 with the maximum diameter at the distal end 12 fully expands the main bodies of the leaflets (the landing zone of the TAVR valve) to achieve the reshaping effect, allowing the TAVR valve to be stably released and well expanded. As shown in FIG. 4c, a tapering portion of the balloon 10 at the distal end 12 is located at the level of the annulus 24 and the left ventricular outflow tract, which has a smaller diameter than the annulus 24 and the left ventricular outflow tract and thus would not contact the annulus 24 and the left ventricular outflow tract during expansion. Therefore, even in the presence of severe calcification of the annulus 24 and the left ventricular outflow tract, there is a little risk of damage to the annulus 24 and the left ventricular outflow tract during expansion (theoretically much lower than the risk of damage to the annulus and the left ventricular outflow tract during expansion in case of using a conventional cylindrical balloon).

Figure 5:
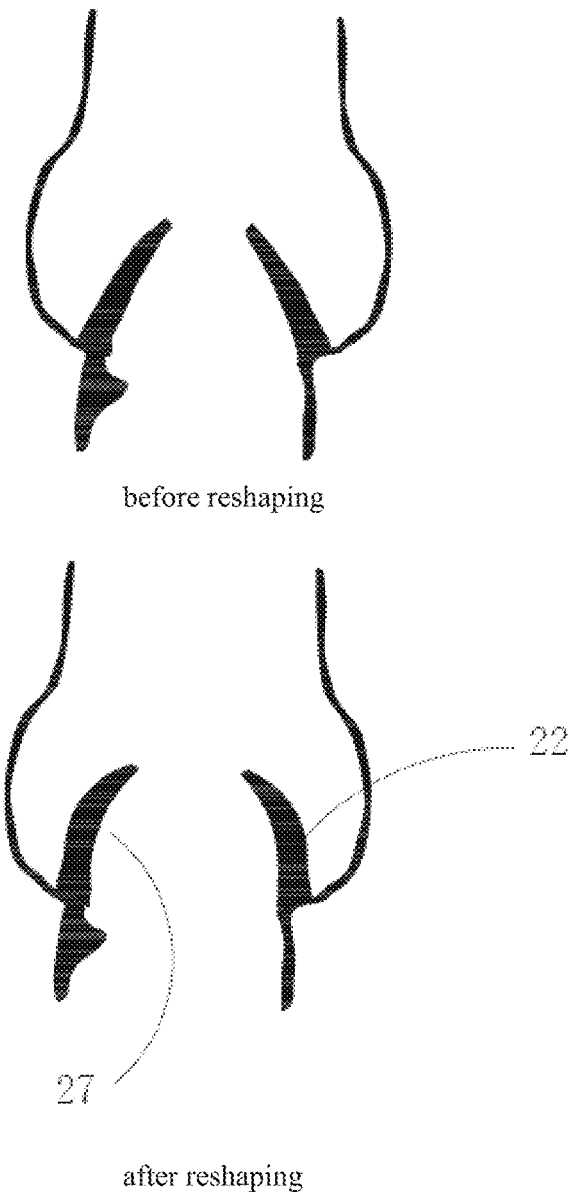
FIG. 5 schematically shows the morphologies of a severely stenosed aortic valve having leaflets with bicuspid malformation and severe calcification before and after reshaping using the method of the present disclosure.

Referring to FIG. 5, before reshaping of the severely stenosed aortic valve having leaflets with bicuspid malformation and severe calcification, the spatial structure of the leaflets is in the shape of a "volcanic vent" and the leaflets, as a whole, is approximately in the shape of a normal cone. After expansion of the aortic valve using the method of the present disclosure, the compliance of the aortic valve is improved, and the inner surfaces of the valve leaflets 22 are in the shape of a concaved arc, forming a space 28 compliant to the self-expandable interventional valve for release. In this embodiment, the space 28 has an approximately ellipsoidal shape.

Figure 7:
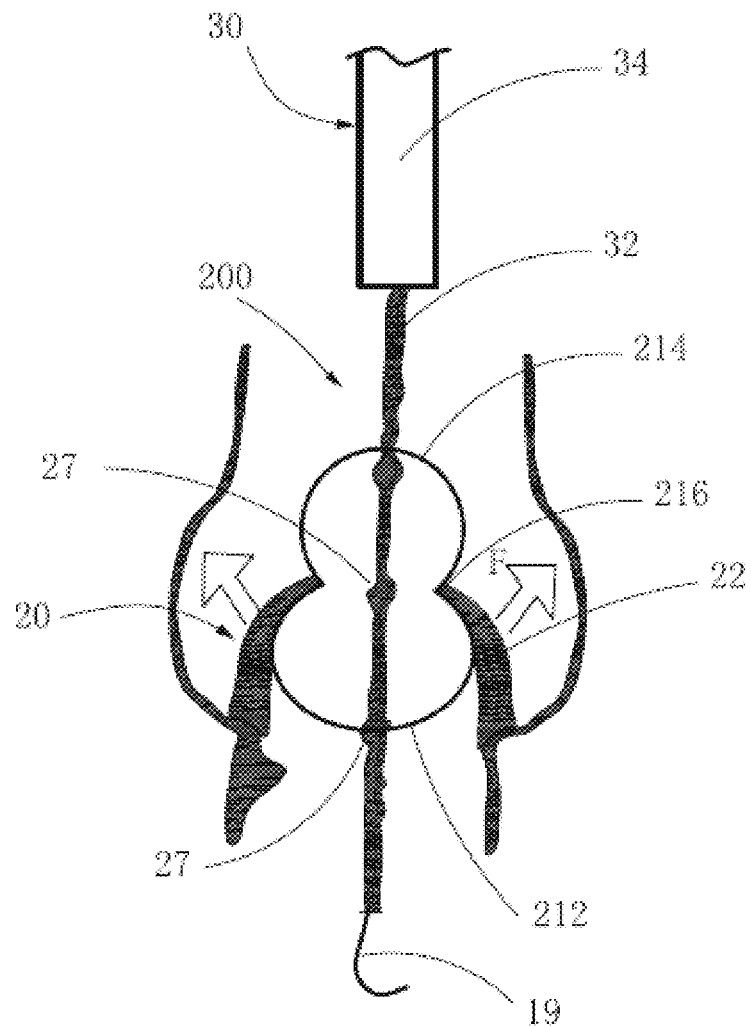
FIG. 7 is a schematic view showing the method of reshaping the leaflets of the aortic valve using the expandable balloon according to a second embodiment.
Figure 8:
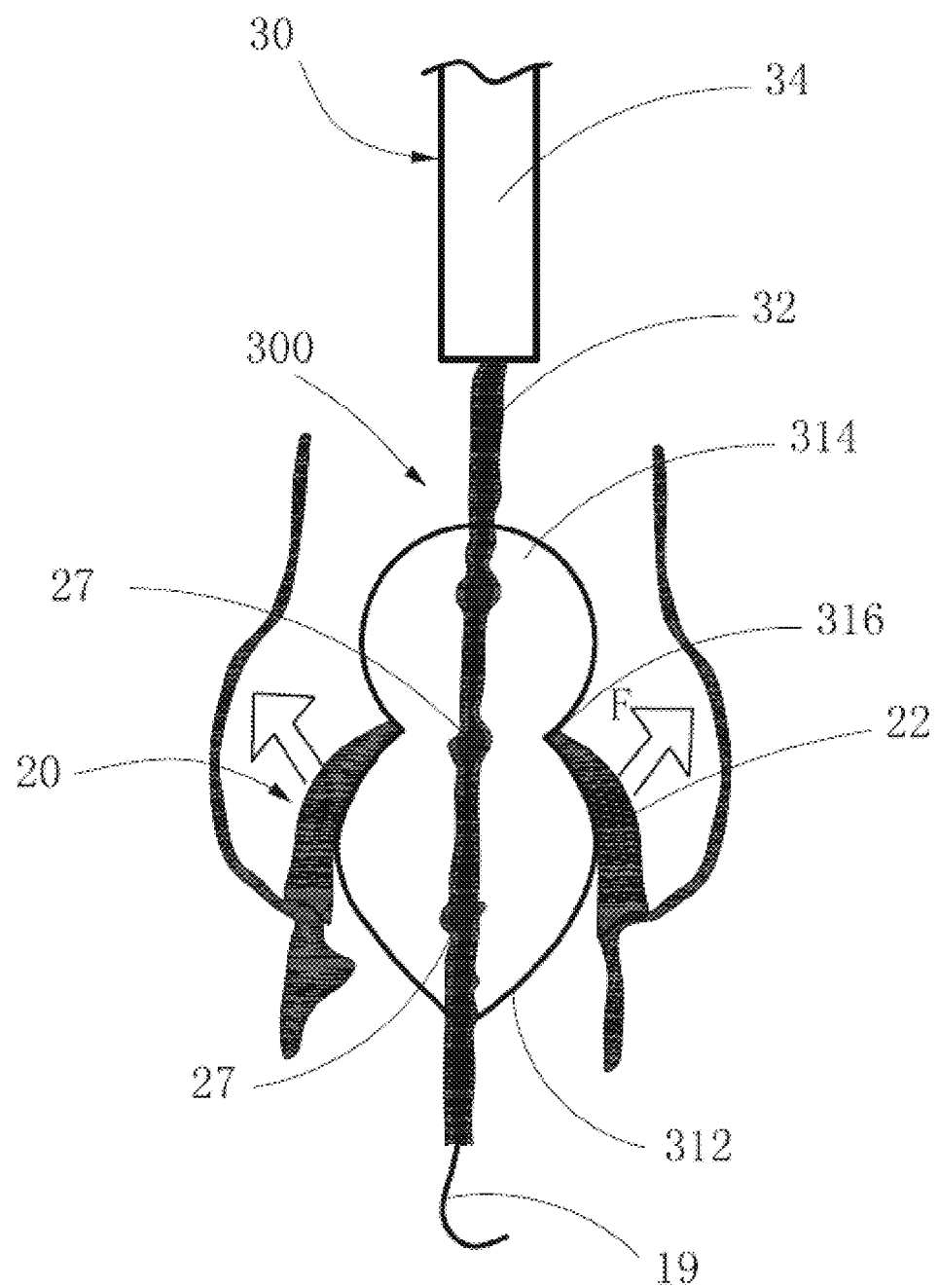
FIG. 8 is a schematic view showing the method of reshaping the leaflets of the aortic valve using the expandable balloon according to a third embodiment.
Figure 9:
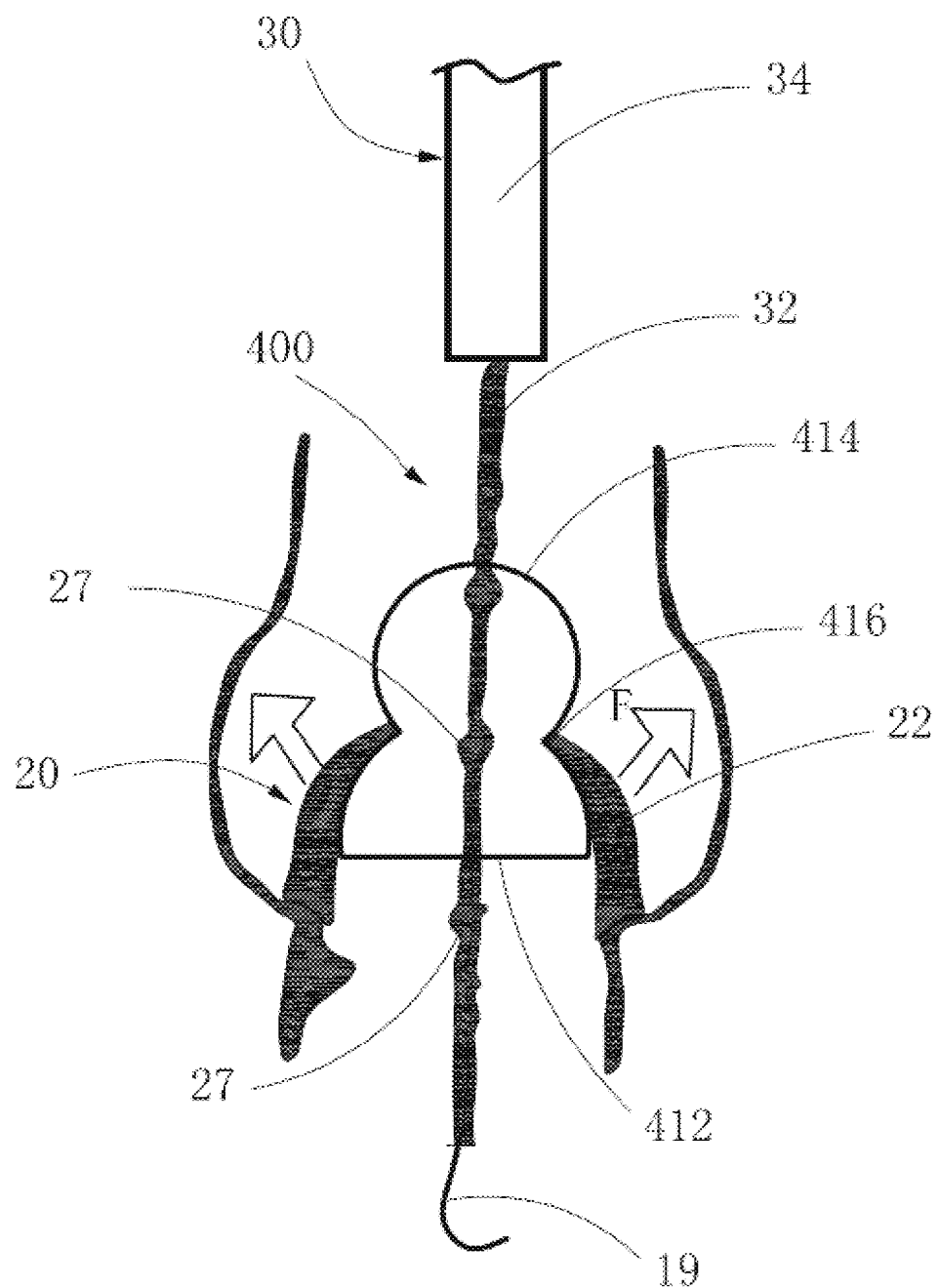
FIG. 9 is a schematic view showing the method of reshaping the leaflets of the aortic valve using the expandable balloon according to a fourth embodiment.

In the embodiment described above, both the distal end 12 and the proximal end 14 of the expanded balloon 10 are ellipsoidal. Alternatively, the proximal end of the balloon does not need to be ellipsoidal, and may have other shapes, providing that its fully expanded size is larger than the size of the orifice so that it cannot pass through the orifice after expansion. The distal end of the balloon does not need to be ellipsoidal, either, and may have other shapes. FIGS. 7 to 9 show alternative balloons for reshaping the aortic valve in other embodiments.

Specifically, in the embodiment shown in FIG. 7, the distal end 212 of the balloon 200 is also ellipsoidal, and different from the above-described embodiment in: the major axis of the ellipsoid of the balloon 200 at the distal end 212 in this embodiment is perpendicular to the axis of the balloon 200, and the minor axis of the ellipsoid coincides with the axis of the balloon 200. The distal end 212 of the balloon 200 in this embodiment can also provide a non-radial abutment force to the main bodies of the leaflets of the aortic valve 20 to expand the main bodies of the leaflets upward and outward to reshape the leaflets of the aortic valve 20, thereby improving the compliance of the leaflets. After being expanded by the distal end 212 of the balloon 200 in this embodiment, the reshaped aortic valve 20 has concaved arcs therein, thereby forming a space compliant to the self-expandable interventional valve for release. In addition, the proximal end 214 of the balloon 200 in this embodiment has a standard spherical shape. The waist 216 with a smaller diameter between the proximal end 214 and the distal end 212 moderately expands the orifice of the aortic valve 20 during expansion.

In the embodiment shown in FIG. 8, the distal end 312 of the balloon 300 is drop-like. The drop-like distal end 312 can also provide a non-radial abutment force to the main bodies of the leaflets of the aortic valve 20 during expansion of the balloon 300 to expand the main bodies of the leaflets upward and outward to reshape the leaflets of the aortic valve 20, thereby improving the compliance of the leaflets. After being expanded by the distal end 312 of the balloon 300 in this embodiment, the reshaped aortic valve 20 has concave arcs therein, thereby forming a space compliant to the self-expandable interventional valve for release. In addition, the proximal end 314 of the balloon 300 in this embodiment also has a standard spherical shape. The waist 316 with a smaller diameter between the proximal end 314 and the distal end 312 moderately expands the orifice of the aortic valve 20 during expansion.

In the embodiment shown in FIG. 9, the distal end 412 of the balloon 400 has a semispherical shape. The semispherical distal end 412 can also provide a non-radial abutment force to the main bodies of the leaflets of the aortic valve 20 during expansion of the balloon 400 to expand the main bodies of the leaflets upward and outward to reshape the leaflets of the aortic valve 20, thereby improving the compliance of the leaflets. After being expanded by the distal end 412 of the balloon 400 in this embodiment, the reshaped aortic valve 20 has a concaved hemispherical shape therein, thereby forming a space compliant to the self-expandable interventional valve for release. In addition, the proximal end 414 of the balloon 400 in this embodiment also has a standard spherical shape. The waist 416 with a smaller diameter between the proximal end 414 and the distal end 412 moderately expands the orifice of the aortic valve 20 during expansion.

Figure 6:
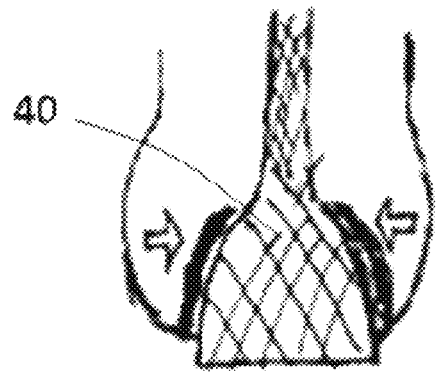
FIG. 6 schematically shows the positional relationship between a prosthetic valve stent implanted via a TAVR procedure and a native aortic valve after the native aortic valve is expanded using the method of the present disclosure.

Furthermore, it may be preferred to immediately perform the TAVR procedure to implant the self-expandable interventional valve following the method of the present disclosure of reshaping the aortic valve. Referring to FIG. 6, the force applied by the reshaped aortic valve on the self-expandable interventional valve 40 during the release process is significantly reduced, and the self-expandable interventional valve 40 is released stably without obvious displacement, thereby reducing the possibility of implanting another valve and the risk of significant perivalvular leakage and severe conduction block and the like, improving the success rate of the implanted device. Since the leaflets are reshaped and have improved compliance, depending on the size of the patient's annulus, a TAVR valve with a matched model can be selected to reduce residual pressure difference and patient-prosthetic valve mismatch, thereby improving the long-term prognosis for the patient and allowing a further treatment via TAVR (valve in valve) in the case of valvular failure in the long term.

The method of the present disclosure may also be used in combination with the following steps: (1) fragmenting the calcified mass, the calcified fusion crest, and the calcified commissure at any portions of the BAV leaflets through intravascular ultrasound, to remove the limiting structure and improve the compliance of the leaflets, (2) cutting the calcified portions of the main bodies and free edges of the BAV leaflets by mechanical cutting to improve the compliance of the leaflets.

What is claimed is:

1. A method of reshaping a stenosed aortic valve having leaflets with bicuspid malformation and calcification, comprising:
    delivering a balloon to the aortic valve, wherein the balloon comprises an expandable distal end, an expandable proximal end, and a waist between the distal end and the proximal end, in an expanded state of the balloon, the waist has a smaller size than the distal end and the proximal end;
    positioning the balloon in such a manner that the distal end of the balloon is aligned with the leaflets, the waist is aligned with the orifice of the aortic valve, and the proximal end is located outside of the aortic valve;
    expanding the balloon so that the distal end of the balloon is expanded to push the leaflets upward from a bottom of the aortic valve to reshape the leaflets, and
    forming a space compliant to a self-expandable interventional valve for release,
    wherein a force to main bodies of the leaflets from the expanded balloon is greater than a force to the orifice of the aortic valve from the expanded balloon; and
    wherein a maximum force to the leaflets from the expanded balloon is located at a position of 2-8 mm distant from the annulus along a direction from the annulus towards to the orifice.

2. The method of claim 1, wherein the distal end of the balloon is configured to abut the bottom side of the aortic valve after being expanded, and support and expand the leaflets outwardly and proximally in a direction at an acute angle to a proximal end of an axis of the balloon.

3. The method of claim 2, wherein the acute angle is in a range of 20-70 degrees.

4. The method of claim 2, wherein the acute angle is in a range of 30-60 degrees.

5. The method of claim 2, wherein the direction is substantially perpendicular to the main bodies of the leaflets.

6. The method of claim 1, wherein the distal end of the balloon is configured to support and expand the leaflets for 3-5 seconds after being expanded.

7. The method of claim 1, wherein the force to the orifice from the expanded balloon is greater than a force to the annulus of the aortic valve from the expanded balloon.

8. The method of claim 1, wherein a force to the annulus from the expanded balloon is zero.

9. The method of claim 1, wherein the reshaped leaflets of the aortic valve have a concaved arc-shaped inner surface.

10. The method of claim 1, wherein materials of the waist and the proximal end of the balloon are more compliant than a material of the distal end of the balloon.

11. The method of claim 10, wherein, when the balloon is expanded, the balloon is first inflated at a first pressure so that the distal end is fully expanded, and the proximal end has a smaller diameter than the orifice at the first pressure, and the balloon is continually inflated at a second pressure so that the proximal end is fully expanded, wherein the second pressure is greater than the first pressure.

12. The method of claim 1, wherein the maximum diameter of the distal end of the balloon is greater than or equal to the maximum diameter of the proximal end of the balloon.

13. The method of claim 1, wherein the balloon is loaded into a delivery system prior to the delivering, and the delivery system delivers the balloon to the aortic valve via a trans-femoral puncture course.

14. The method of claim 1, wherein the distal end of the expanded balloon is spherical, hemispherical, ellipsoidal or drop-like.

15. The method of claim 1, wherein the balloon further comprises at least one marker for indicating position of the balloon.

* * * * *